(12) United States Patent
Smith

(10) Patent No.: US 8,187,322 B2
(45) Date of Patent: May 29, 2012

(54) DRUG ELUTING STENT AND METHOD OF MAKING THE SAME

(75) Inventor: Scott R. Smith, Chaska, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/047,051

(22) Filed: Mar. 14, 2011

(65) Prior Publication Data

US 2011/0166646 A1 Jul. 7, 2011

Related U.S. Application Data

(63) Continuation of application No. 12/051,304, filed on Mar. 19, 2008.

(51) Int. Cl.
*A61F 2/06* (2006.01)
(52) U.S. Cl. .............. 623/1.42; 623/1.44; 623/1.39; 623/1.45; 623/1.46
(58) Field of Classification Search .............. 623/1.39, 623/1.42, 1.44, 1.46
See application file for complete search history.

(56) References Cited

U.S. PATENT DOCUMENTS

| | | | |
|---|---|---|---|
| 5,735,897 A | 4/1998 | Buirge | |
| 5,843,172 A | 12/1998 | Yan | |
| 5,858,556 A | 1/1999 | Eckert et al. | |
| 5,972,027 A | 10/1999 | Johnson | |
| 6,099,562 A | 8/2000 | Ding et al. | |
| 6,253,443 B1 | 7/2001 | Johnson | |
| 6,284,305 B1 | 9/2001 | Ding et al. | |
| 6,312,463 B1 | 11/2001 | Rourke et al. | |
| 6,471,721 B1 | 10/2002 | Dang | |
| 6,545,097 B2 | 4/2003 | Pinchuk et al. | |
| 6,620,192 B1 | 9/2003 | Jalisi | |
| 6,620,194 B2 | 9/2003 | Ding et al. | |
| 6,623,520 B2 | 9/2003 | Jalisi | |
| 6,676,701 B2 | 1/2004 | Rourke et al. | |
| 6,723,120 B2 | 4/2004 | Yan | |
| 6,770,086 B1 | 8/2004 | Girton | |
| 6,790,228 B2 | 9/2004 | Hossainy et al. | |
| 6,855,770 B2 | 2/2005 | Pinchuk et al. | |
| 6,865,810 B2 | 3/2005 | Stinson | |
| 6,899,731 B2 | 5/2005 | Li et al. | |
| 6,904,658 B2 | 6/2005 | Hines | |
| 7,014,654 B2 | 3/2006 | Welsh et al. | |
| 7,041,129 B2 | 5/2006 | Rourke et al. | |
| 7,056,339 B2 | 6/2006 | Elkins et al. | |
| 7,063,720 B2 | 6/2006 | Iki et al. | |
| 7,105,018 B1 | 9/2006 | Yip et al. | |
| 7,105,175 B2 | 9/2006 | Schwarz | |
| 7,144,422 B1 | 12/2006 | Rao | |
| 7,235,096 B1 | 6/2007 | Tassel et al. | |
| 7,955,383 B2 * | 6/2011 | Krivoruchko et al. | ....... 623/1.44 |

(Continued)

FOREIGN PATENT DOCUMENTS

WO 0249536 6/2002

(Continued)

*Primary Examiner* — Thomas J Sweet
*Assistant Examiner* — Seema Swaminathan
(74) *Attorney, Agent, or Firm* — Vidas, Arrett & Steinkraus, P.A.

(57) ABSTRACT

A drug eluting stent comprising a multilayer tubular structure which includes at least one intermediate layer having reservoirs therein for deposition of a drug, the intermediate layer eluting drug in a lateral direction, and methods of making the same.

20 Claims, 4 Drawing Sheets

U.S. PATENT DOCUMENTS

| | | |
|---|---|---|
| 2001/0029660 A1 | 10/2001 | Johnson |
| 2004/0000046 A1 | 1/2004 | Stinson |
| 2004/0215169 A1 | 10/2004 | Li |
| 2005/0271701 A1 | 12/2005 | Cottone, Jr. et al. |
| 2006/0093643 A1 | 5/2006 | Stenzel |
| 2006/0121080 A1 | 6/2006 | Lye et al. |
| 2006/0193886 A1 | 8/2006 | Owens et al. |
| 2006/0193887 A1 | 8/2006 | Owens et al. |
| 2006/0193888 A1 | 8/2006 | Lye et al. |
| 2006/0193889 A1 | 8/2006 | Spradlin et al. |
| 2006/0193890 A1 | 8/2006 | Owens et al. |
| 2006/0222679 A1 | 10/2006 | Shanley et al. |
| 2007/0198081 A1* | 8/2007 | Castro et al. ............... 623/1.42 |
| 2007/0208415 A1 | 9/2007 | Grotheim et al. |
| 2008/0147177 A1* | 6/2008 | Scheuermann et al. ..... 623/1.42 |
| 2008/0312736 A1* | 12/2008 | Mueller et al. ............ 623/1.46 |
| 2009/0132023 A1* | 5/2009 | Sieradzki et al. ........... 623/1.15 |
| 2009/0192593 A1* | 7/2009 | Meyer et al. ............... 623/1.42 |
| 2010/0063584 A1* | 3/2010 | Holman et al. ............ 623/1.44 |

FOREIGN PATENT DOCUMENTS

| | | |
|---|---|---|
| WO | 2004091444 | 10/2004 |
| WO | 2005030094 | 4/2005 |
| WO | 2006065665 | 6/2006 |

\* cited by examiner

DRUG ELUTING STENT AND METHOD OF MAKING THE SAME

CROSS-REFERENCE TO RELATED APPLICATIONS

This application is a Continuation of U.S. patent application Ser. No. 12/051,304, filed Mar. 19, 2008, the entire disclosure of which is hereby incorporated herein by reference.

FIELD OF THE INVENTION

The present invention relates to the field of implantable medical devices, in particular stents, and to methods of loading such devices with therapeutic agents.

BACKGROUND OF THE INVENTION

Stents, grafts, stent-grafts, vena cava filters, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, peripheral or secondary vessels, etc.

Stents may be used to reinforce body vessels and to prevent restenosis following angioplasty in the vascular system in order to maintain vascular patency and thus reduce the likelihood of thrombosis and restenosis which may occur after the procedure, requiring another angioplasty procedure or a surgical bypass operation.

Stents are expandable frameworks, usually cylindrical or tubular in shape, functioning to physically hold open, and if desired, to expand the wall of a vessel lumen. One common design is stents formed of a series of circumferential bands, each band formed of interconnected stent struts. Typically, stents are radially compressed or crimped for insertion through small body lumens via catheter assemblies, and are then expanded to a larger diameter once at the treatment site. Stents come in a variety of configurations and may be self-expanding, expanded by an internal radial force, such as when mounted on a balloon, or a combination of self-expanding and balloon expandable (hybrid expandable).

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. To treat this condition, additional revascularization procedures are frequently required, thereby increasing trauma and risk to the patient.

One of the techniques recently introduced to address the problem of restenosis is the use of drug eluting coatings on stent surfaces which include various pharmacologically active therapeutic agents on stents. Such coatings, however, can provide little actual control over the release kinetics of beneficial agents.

Control of the rate and uniformity of the drug elution of a stent is considered to be very important. It has also been found to be beneficial to provide a luminal stent surface having some surfaces with different drug effects than other surfaces. Furthermore, restenosis may not occur at the same rate or level in all regions of a vessel. For example, restenosis may not occur at the same rate or level in all regions of a bifurcated vessel. Therefore, it may be beneficial in the case of a vessel bifurcation to optimize the drug dosage in specific, high risk restenosis regions within a bifurcated lesion.

It has also been observed that higher drug concentration can occur in the center of the abluminal surfaces of the stent. This may be due to inhibition of normal intra mural transport due to the barrier presented by the stent itself, and the compression of the vessel wall behind the stent struts. This may also be due to more rapid protein deposition around the struts of the stent after implantation, particularly in the space between the lateral surface of the stent and the vessel wall.

There remains a need in the art for a stent system in which the drug dosage can be optimized in specific regions of the stent surface.

There remains a need in the art for a stent system in which the drug dosage can be optimized in specific, high risk restenosis regions within a bifurcated lesion.

Without limiting the scope of the invention a brief summary of some of the claimed embodiments of the invention is set forth below. Additional details of the summarized embodiments of the invention and/or additional embodiments of the invention may be found in the Detailed Description of the Invention below.

SUMMARY OF THE INVENTION

In one aspect, the present invention relates to a stent having lateral surfaces that are adapted to receive a pharmacologically active therapeutic agent.

In one aspect, the present invention relates to a method of loading lateral stent surfaces with a beneficial therapeutic agent.

In one embodiment, a porous intermediate layer is loaded with a beneficial therapeutic agent.

The porous intermediate layer may be formed with a sintered porous powdered metal.

In another embodiment, the lateral wall of the central layer comprises cavities or channels into which a drug is deposited.

The cavities of channels can be created by selective etching of the intermediate layer of a multilayer structure which includes a support layer having the intermediate layer disposed thereon, and a covering layer disposed on the intermediate layer.

These and other aspects, embodiments and advantages of the present invention will be apparent to those of ordinary skill in the art upon review of the Detailed Description and Claims to follow.

DETAILED DESCRIPTION OF THE INVENTION

While this invention may be embodied in many different forms, there are described in detail herein specific embodiments of the invention. This description is an exemplification of the principles of the invention and is not intended to limit the invention to the particular embodiments illustrated.

All published documents, including all US patent documents, mentioned anywhere in this application are hereby expressly incorporated herein by reference in their entirety. Any copending patent applications, mentioned anywhere in this application are also hereby expressly incorporated herein by reference in their entirety.

In one aspect, the present invention relates to a multilayer stent having a porous intermediate layer wherein the intermediate layer includes at least one porous material and at least one drug. The multilayer stent further includes a support layer and a covering layer. The multilayer stent is constructed so that the intermediate porous layer elutes drug in a lateral direction.

Figure 1:
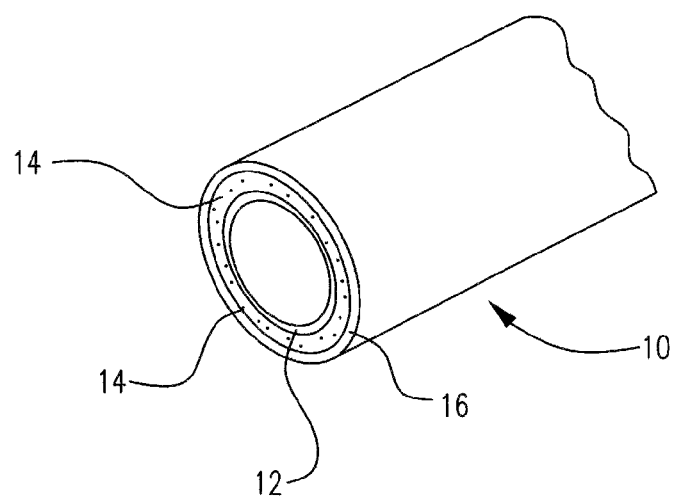
FIG. 1 is a partial perspective view of one embodiment of a multilayer tubular structure according to the invention.

Turning now to the figures, wherein like numerals indicate like elements, FIG. 1 is a partial perspective view of a multilayer tubular structure 10 from which a stent may be constructed, the multilayer tubular structure 10 having an inner or support layer 12, an intermediate porous layer 14, and an outer or covering layer 16.

Support layer 12 and covering layer 16 may be formed from any suitable material employed in the manufacture of such medical devices. Support layer 12 and covering layer 16 may be formed from the same or different material.

Suitable materials for the support and/or covering layer include, but are not limited to, metals and metal alloys. Preferably, such metal or metal alloys are biocompatible. Specific examples include, but are not limited to, stainless steel, for example 316L stainless steel, and enriched stainless steel such as those enriched with platinum group metals such as platinum (PERSS®), palladium, rhodium, iridium, ruthenium, rhenium, gold, silver, and osmium, for example.

Other suitable metals and metal alloys include, but are not limited to, cobalt chromium alloy (ELGILOY®) available from Elgiloy Specialty Metals in Elgin, Ill.), platinum-iridium alloy, tantalum, gold, magnesium, tungsten, molybdenum, etc.

Suitable shape memory metals include, but are not limited to, nickel-titanium alloys also referred to as NiTinol (ELASTINITE®)), copper-zinc-aluminum and copper-aluminum-nickel.

In one embodiment, support layer 12 is selected from stainless steel 316L and covering layer 16 is also selected from stainless steel 316L.

In another embodiment, support layer 12 is selected from platinum-enhanced stainless steel (PERSS®) and covering layer 16 is also selected from platinum-enhanced stainless steel (PERSS®).

In one aspect, of the invention, intermediate drug eluting layer 14 is a porous layer, and may be formed from any suitable material containing a plurality of cavities into which a drug containing material may be deposited. Suitably, the intermediate layer is selected so as to elute drug at a faster kinetic rate than the support layer 12 or the covering layer 16. Suitably, the covering layer 12 and the support layer 16 are substantially non-porous and elute substantially no drug.

The porous layer may be metal or metal alloy, suitably a biocompatible metal or metal alloy. The porous layer may be selected from the same metals or metal alloys as the covering layer and/or support layer as discussed above, and may be the same as or different than the covering layer and/or support layer.

For example, in the embodiment wherein the support layer 12 and the covering layer 16 are stainless steel, the porous layer may also be formed from stainless steel. However, some other metal may be selected as well. For example, radiopaque metals such as ruthenium (Ru), rhodium (Rd), palladium (Pd), osmium (Os), iridium (Ir), platinum (Pt), silver (Ag), and gold (Au), tantalum (Ta), rhenium (Re), and so forth, molybdenum, iodine and its salts or compounds, barium and its salts or compounds, bismuth and its salts or compounds, tungsten, and so forth. In some preferred embodiments, the intermediate porous layer is stainless steel, gold or titanium.

In one embodiment, the intermediate porous layer is formed from iridium oxide (IrOx).

Polymers and/or ceramics may also be employed in forming the porous intermediate layer, as well as combinations of polymers and/or ceramics with metal or metal alloys.

The intermediate layer 14 may be provided with its porosity, i.e. cavities or pores, using any suitable method of creating a porous material.

For example, the porous material may be created by sintering a powdered metal, the resultant product of which is referred to in the art as a "porous sintered metal".

Sintering generally involves fusing small particles of metal using heat and/or pressure to weld them together. A porous sintered metal layer may be formed by providing a powdered metal, sintering the powdered metal into a tubular form, and then drawing the sintered powdered metal tube with an inner and outer tube to form the multilayer tubular structure. Powdered metals are typically available with a particle size of about 40 microns or less. Suitably, powdered metals having a particle size between about 5 to about 15 microns will be used. Pore size is controlled by the particle size of the powdered metal. Suitably, mean pore size is about 10 microns or less. Suitably the powdered metals also have a high void fraction and low density. High void fraction may be obtained with shapes such as hollow spheres, cylinders, rings, saddles or honeycomb-type structures.

The pores are suitably continuous in the axial (along the same line as an axis or centerline) and/or circumferential directions to permit elution.

Pores may extend through the entire thickness of the central layer, for example, up to about 20 microns or so, although this may vary according to the thickness of the central layer.

Pores may also be created in the intermediate layer by texturing or patterning the mating surfaces of the inner and/or outer layers (suitably the outer surface of the inner member) without a discrete intermediate layer. For examples, grooves, pits and bumps, and so forth may be created during drawing, chemical etching, physical etching, etc. can also generate a texture.

Figure 2:
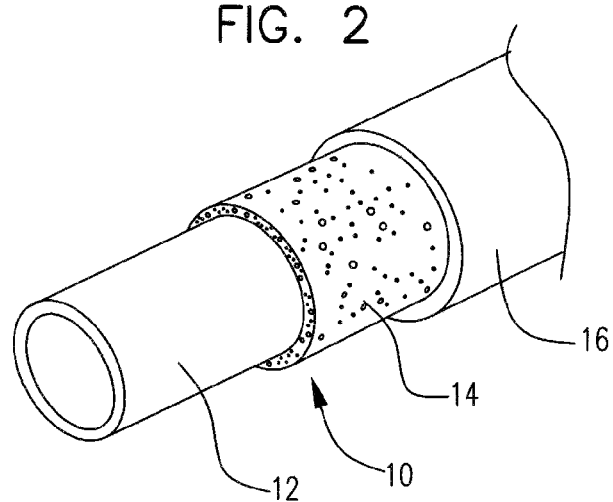
FIG. 2 is an alternative partial perspective view with parts exploded of a multilayer tubular structure similar to that shown in FIG. 1.

A fragmentary partial cutaway view of the multilayer tubular structure similar to that shown in FIG. 1 is shown in FIG. 2.

Porous sintered powdered metals are known in the art. For example, see commonly assigned U.S. Pat. Nos. 5,972,027 and 6,253,443, each of which is incorporated by reference herein in its entirety. See also U.S. Pat. No. 5,843,172, the entire content of which is incorporated by reference.

Alternatively, the powdered metal may be mixed with a binding agent and coated onto an inner tube, sintered, and then drawn with an outer tube. The binding agent may then be baked off.

The porous intermediate layer may also be selectively applied to the support layer. For example, it may be desirable to apply the porous intermediate layer at only the distal and/or proximal end of the tubular structure, or at the central portion of the tubular structure. Such selective application of the porous intermediate layer may result, after cutting a stent pattern into the tubular structure, in a stent which, elutes drugs from selected portions of the stent structure. Such selective application of the porous intermediate drug eluting layer may be beneficial for bifurcated stents, for example. When lesions occur at a bifurcated vessel, it is not uncommon to have higher restenosis in some areas of the bifurcation than others. Thus, in such an embodiment, the drug eluting layer may be selectively positioned so as to control the amount of drug release at specific locations within a body lumen. For example, it may be desirable for lateral elution of the drug around the side branch opening of the bifurcated stent. See, for example, commonly assigned copending U.S. patent application Ser. No. 11/368,932, filed Mar. 6, 2006, the entire content of which is incorporated by reference herein in its entirety.

Figure 3:
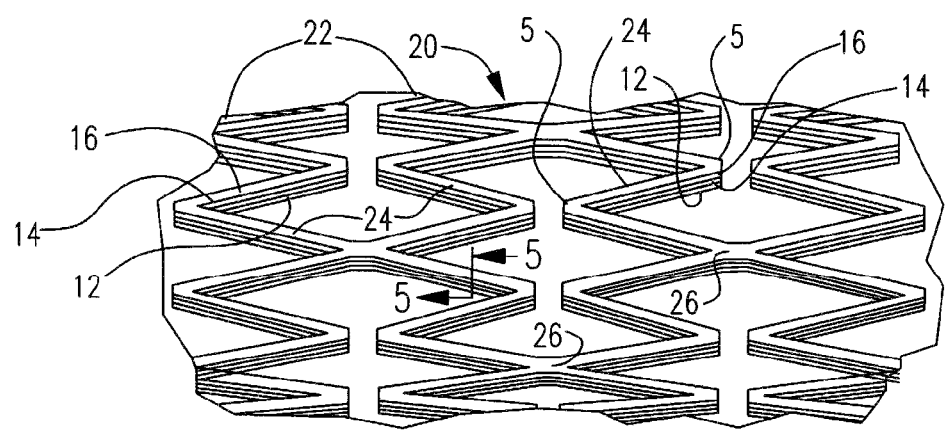
FIG. 3 is a partial perspective view of a multilayer stent according to the invention.

Once the multilayer tubular structure is formed with the at least one support layer 12, the at least one intermediate layer 14, and the at least one covering layer 16, the structure is then ready for formation of a stent pattern therein. This may be accomplished using any suitable method known in the art such as with etching or laser cutting. An example of a stent 20 which may be formed according to the invention is shown as a partial perspective view in FIG. 3. Stent 20 has a multilayer structure with support layer 12, a porous intermediate layer 14 and a covering layer 16. In this example, stent 20 is shown having a plurality of serpentine bands 22 formed of a plurality of struts interconnected by connector elements 26. The stent shown in FIG. 3 is intended for illustrative purposes only. Any stent configuration may be employed, however.

Cleaning, etching and electropolishing is beneficial for helping to ensure that the cavities remain open after stent cutting. Furthermore, additional compression and heating steps may be applied to achieve diffusion bonding between the layers.

The drug is suitably loaded into the porous material at this time. However, the drug may be loaded at any stage during the process.

The terms, "drug", "therapeutic agent", "pharmaceutically active agent", "pharmaceutically active material", "beneficial agent", "bioactive agent", and other related terms may be used interchangeably herein and include genetic therapeutic agents, non-genetic therapeutic agents and cells. A drug may be used singly or in combination with other drugs. Drugs include genetic materials, non-genetic materials, and cells.

Examples of non-genetic therapeutic agents include, but are not limited to, anti-thrombogenic agents, anti-proliferative agents, anti-inflammatory agents, analgesics, antineoplastic/antiproliferative/anti-miotic agents, anesthetic agents, anti-coagulants, vascular cell growth promoters, vascular cell growth inhibitors, cholesterol-lowering agents; vasodilating agents; and agents which interfere with endogenous vascoactive mechanisms.

Genetic agents include anti-sense DNA and RNA and coding DNA, for example.

Cells may be of human origin, animal origin, or may be genetically engineered.

Examples of anti-thrombogenic agents include, but are not limited to, heparin, heparin derivatives, urokinase, and PPack (dextrophenylalanine proline arginine chloromethylketone).

Examples of anti-proliferative agents include, but are not limited to, enoxaprin, angiopeptin, or monoclonal antibodies capable of blocking smooth muscle cell proliferation, hirudin, acetylsalicylic acid, etc.

Examples of anti-inflammatory agents include steroidal and non-steroidal anti-inflammatory agents. Specific examples of steroidal anti-inflammatory agents include, but are not limited to, budesonide, dexamethasone, desonide, desoximetasone, corticosterone, cortisone, hydrocortisone, prednisolone, etc.

Specific examples of non-steroidal anti-inflammatory agents include, but are not limited to, acetylsalicylic acid (i.e. aspirin), ibuprofen, ibuproxam, indoprofen, ketoprofen, loxoprofen, miroprofen, naproxen, oxaprozin, piketoprofen, pirprofen, pranoprofen, protizinic acid, sulfasalazine, mesalamine, suprofen, tiaprofenic acid, etc.

Examples of analgesics include both narcotic and non-narcotic analgesics. Examples of narcotic analgesics include, but are not limited to, codeine, fentanyl, hydrocodone, morphine, promedol, etc.

Examples of non-narcotic analgesics include, but are not limited to, acetaminophen, acetanilide, acetylsalicylic acid, fenoprofen, loxoprofen, phenacetin, etc.

Examples of antineoplastic/antiproliferative/anti-miotic agents include, but are not limited to, paclitaxel, 5-fluorouracil, cisplatin, vinblastine, vincristine, epothilones, endostatin, angiostatin and thymidine kinase inhibitors.

Examples of anesthetic agents include, but are not limited to, lidocaine, bupivacaine, and ropivacaine, etc.

Examples of anti-coagulants include, but are not limited to, D-Phe-Pro-Arg chloromethyl keton, an RGD peptide-containing compound, heparin, antithrombin compounds, platelet receptor antagonists, anti-platelet receptor antibodies, aspirin, prostaglandin inhibitors, platelet inhibitors and tick antiplatelet peptides.

Derivatives of many of the above mentioned compounds also exist which are employed as therapeutic agents.

Of course mixtures of any of the above may also be employed.

In each embodiment disclosed above, a coating which allows drug to elute, can be applied to the entire stent structure, or to parts of the stent structure.

The above lists are intended for illustrative purposes only, and not as a limitation on the scope of the present invention. Examples of suitable drugs can be found in commonly assigned U.S. Pat. No. 7,105,175, U.S. Pat. No. 7,014,654, U.S. Pat. No. 6,899,731, 6,855,770 and U.S. Pat. No. 6,545,097, each of which is incorporated by reference herein in its entirety, and in commonly assigned U.S. Patent Application Publication No. 2004/0215169, the entire content of which is incorporated by reference herein.

The drug may also be employed in combination with a polymer(s), plasticizer(s) and combinations thereof as well. Suitable polymers include thermoplastic polymers, thermoset polymers, hydrophilic polymers and bioresorbable polymer materials.

Examples include block copolymers of styrene and isoprene (SIS), butadiene (SBS), ethylene/butylene (SEBS), isobutylene (SIBS), ethylene/propylene (SEPS), etc. Diblock copolymers may also find utility herein.

Other block copolymers which may be employed include polyamide-block-ether copolymers such as those available under the tradename of PEBAX® available from Arkema in Philadelphia, Pa., and polyester and copolyester elastomers such as poly(ester-block-ether) elastomers available under the tradename of HYTREL® from DuPont de Nemours & Co. and poly(ester-block-ester)

Other suitable polymer coating materials include, polyolefins, such as ethylene and propylene homopolymers, as well as any copolymers or terpolymers of ethylene and propylene such as ethylene-vinyl acetate copolymers, ethylene (meth) acrylate copolymers, ethylene n-butyl acrylate copolymers, and grafted polyolefins such as maleic anhydride grafted polyethylene or polypropylene, and so forth.

Other suitable polymers which may be employed in the coatings of the invention include, but are not limited to, polyesters, polyamides including nylon 6,6 and nylon 12, polyurethanes, polyethers, polyimides, polycarboxylic acids including polyacrylic acids, (meth)acrylates, cellulosics, polycaprolactams, polyacrylamides, polycarbonates, polyacrylonitriles, polyvinylpyrrolidones, copolymers and terpolymers thereof, etc.

The coating may include bioresorbable polymers. Examples of bioresorbable polymers include, but are not limited to, polyhydroxyalkanoates such as poly(hydroxybutyrate) (PHB), poly(hydroxyvalerate) (PHV) and poly(hydroxybutyrate-co-valerate) (PHBV), polylactones such as polycaprolactone (PCL), poly(L-lactic acid) (PLA), poly(glycolic acid) (PGA), poly(lactide-co-glycolide) (PLGA), polydioxanone, polyorthoesters, polyanhydrides, poly(glycolic acid), poly(D,L-lactic acid), poly(lactide-co-caprolactone), poly(glycolic acid-co-trimethylene carbonate), polydioxanone, polyorthoesters, polyphosphoesters, polyphosphoester urethanes, polyanhydrides, poly(amino acids), polyacrylates, cyanoacrylates, poly(trimethylene carbonate), polyurethanes, poly(iminocarbonate), copoly(etheresters) (e.g. PEO/PLA), polyalkylene oxalates, polyphosphazenes and biomolecules such as fibrin, fibrinogen, starch, collagen, hyaluronic acid, etc., other natural polymers such as alginate, polysaccharides such as dextran and cellulose, etc. and mixtures thereof. Bioresorbable polymers are disclosed in U.S. Pat. Nos. 6,790,228, the entire content of which is incorporated by reference herein.

The above lists are intended for illustrative purposes only, and not as a limitation on the scope of the present invention.

The drug(s), along with polymer and/or solvent if employed, may be deposited in the pores or cavities of the intermediate porous layer 14 using a carrier liquid. Any suitable solvent or cosolvent blend may be selected depending on the choice of polymer(s) and therapeutic agent(s). Suitable examples of solvents include, but are not limited to, toluene, xylene, tetrahydrofuran, hexanes, heptanes, etc. The resultant mixture in a solvent or cosolvent blend may have a solids content of about 0.5% to about 10%, more typically about 1% to about 5%. If a polymer is employed, the ratio of polymer to therapeutic agent may be from about 30:70 to about 99:1, more suitably about 70:30 to about 95:5.

Suitably the therapeutic agent(s) is about 50-100% by weight of the drug eluting composition. The stent pore geometry can provide structural support and control elution rate. However, this is not a limiting amount. The therapeutic agent (s) can be used in much lesser amounts if so desired. The stent pore geometry allows much greater latitude in selecting the amount of therapeutic agent(s) that can be used in the drug eluting composition herein whereas in a typical drug eluting coating, the drug may be present at about 30 wt-% or less, and is often much less, for example no more than about 6 wt-%. The amount of drug(s) can affect both the mechanical properties of the coating as well as the elution rate for typical polymer-based drug eluting coatings.

One method of loading the drug(s), along with polymer and/or solvent if desired, into the pores of the intermediate layer 14 is by exposing the intermediate layer 14 to a liquid bath comprising the at least one drug at high pressure, by placing it in a liquid bath within a chamber, the liquid bath comprising the drug(s), and reducing the pressure within the chamber below ambient pressure or by any other method known in the art. See, for example, U.S. Pat. Nos. 5,972,027 and 6,253,443, each of which is incorporated by reference herein in its entirety. Spraying and injecting of the drug(s) into the intermediate layer may also be employed.

Figure 4:
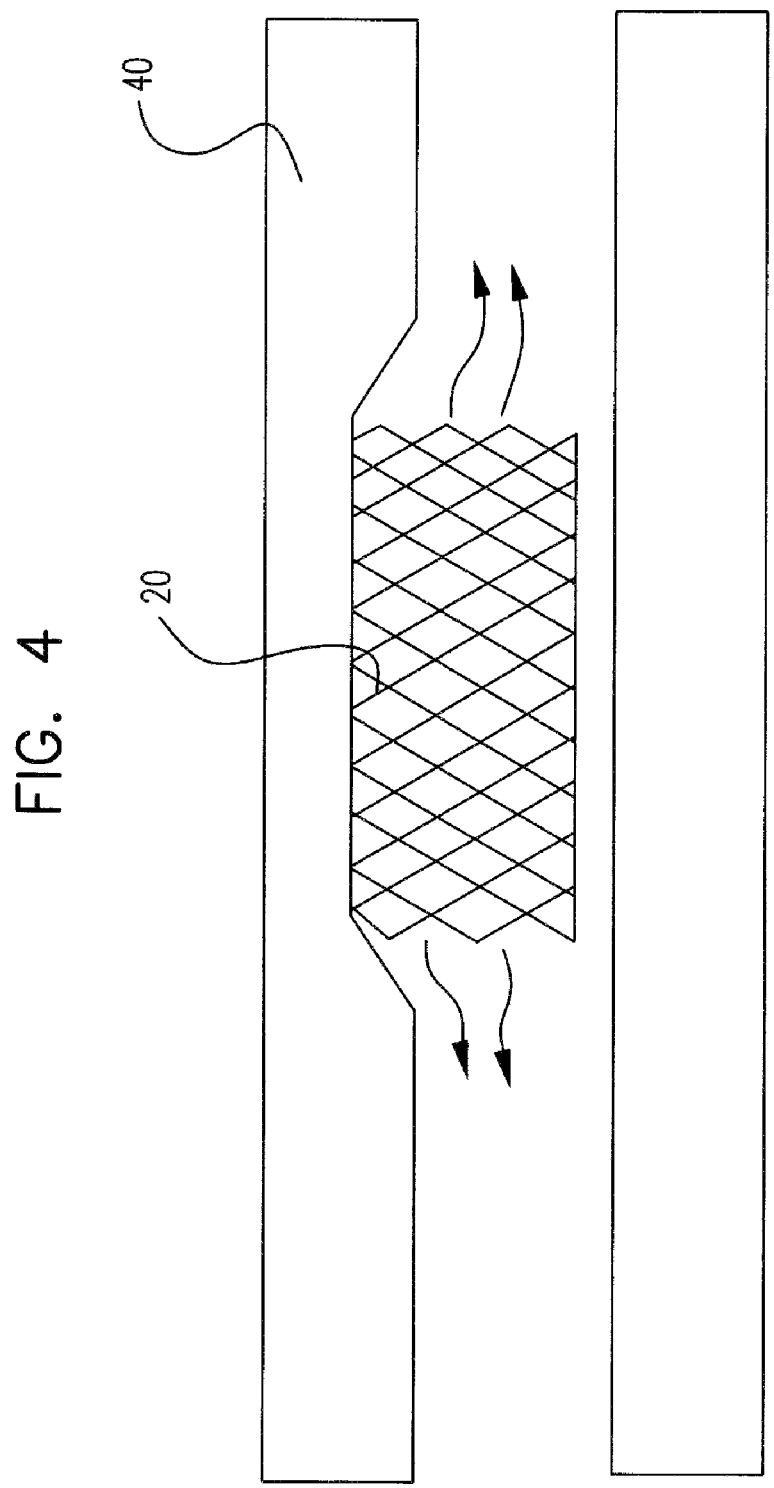
FIG. 4 is a side view of a stent shown within a blood vessel illustrating lateral drug elution.

Intermediate layer 14 elutes drug in a lateral direction from the struts 24 as represented in FIG. 3 by arrows. The term "lateral" as employed herein, shall be used to refer to elution out of the sides of the structure, rather than from the top of bottom of the stent structure, as with a coating of drug eluting material, for example. FIG. 4 is a side view of a stent within shown within a vessel illustrating lateral drug elution.

Figure 5:
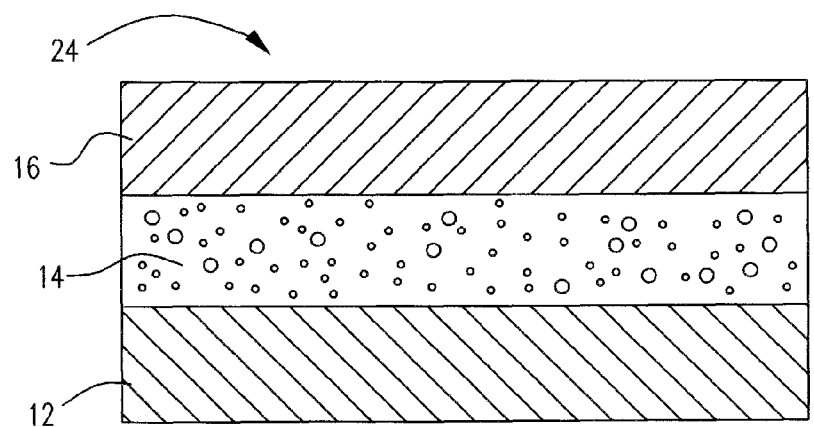
FIG. 5 is a side view of a stent strut taken at section 5-5 in FIG. 3

FIG. 5 is a side view of a stent strut 24 taken at section 5-5 in FIG. 3 showing the multilayer stent structure having the support layer 12, porous intermediate layer 14, and covering layer 16.

Figure 6:
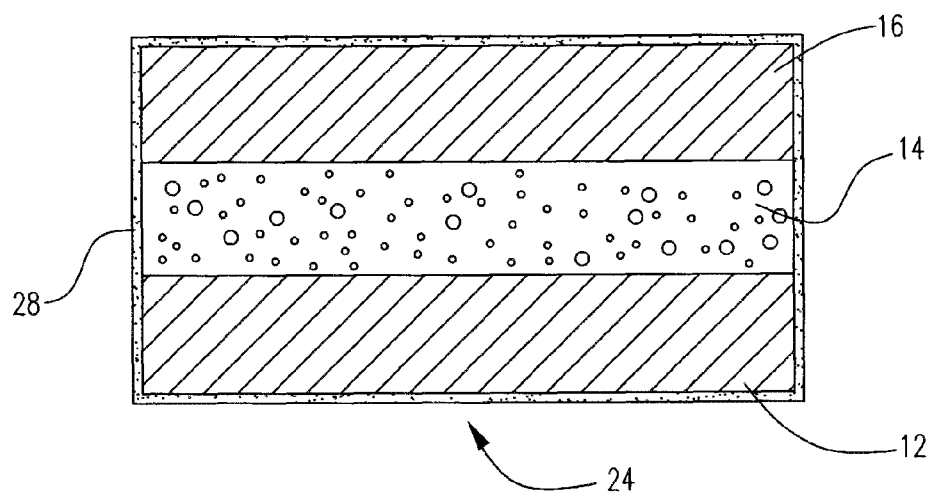
FIG. 6 is a side view of a stent strut similar to that shown in FIG. 5 including a coating thereon.

A coating 28 may be optionally applied to the stent as shown in FIG. 6. Suitable coating materials have been listed above. Some specific examples of coating materials include, but are not limited to, styrenic polymers having styrene endblocks and rubbery midblocks of isobutylene, ethylene/propylene, butadiene, ethylene/butylene, isoprene, etc., ethylene vinyl acetate copolymers, polydimethylsiloxane, polyethylene oxide, polyvinylidene fluoride, copolymers based on ethylene oxide and propylene oxide such as those sold under the tradename of Pluronic® available from BASF North America in Florham Park, N.J., bioresorbable materials such as poly (lactic acid), poly(glycolic acid), polycaprolactone, as well as copolymers of lactide, glycolide and caprolactone, polyanhydrides, polyacrylates, polyurethanes, etc.

The coating is selected so as not to adversely affect the lateral elution of the drug from the stent strut 24.

Figure 7:
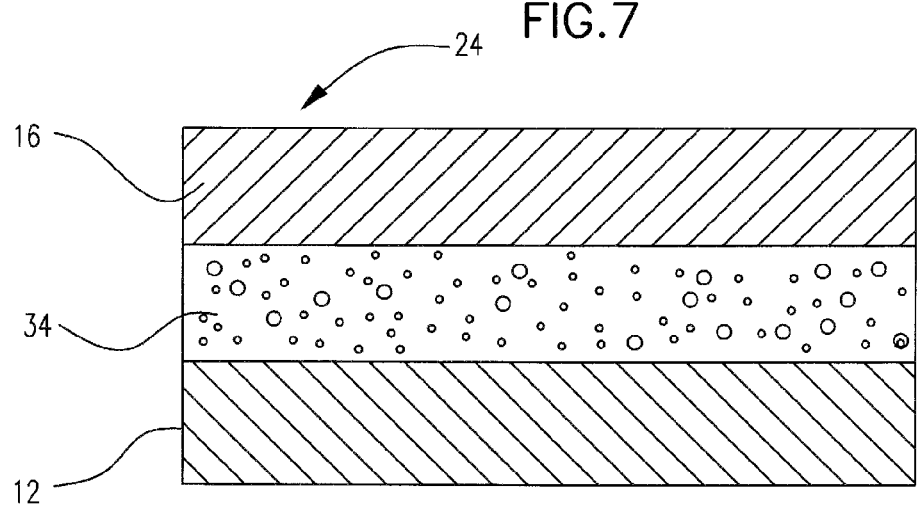
FIG. 7 is a side view of another embodiment of a stent strut wherein the intermediate layer is non-porous.
Figure 8:
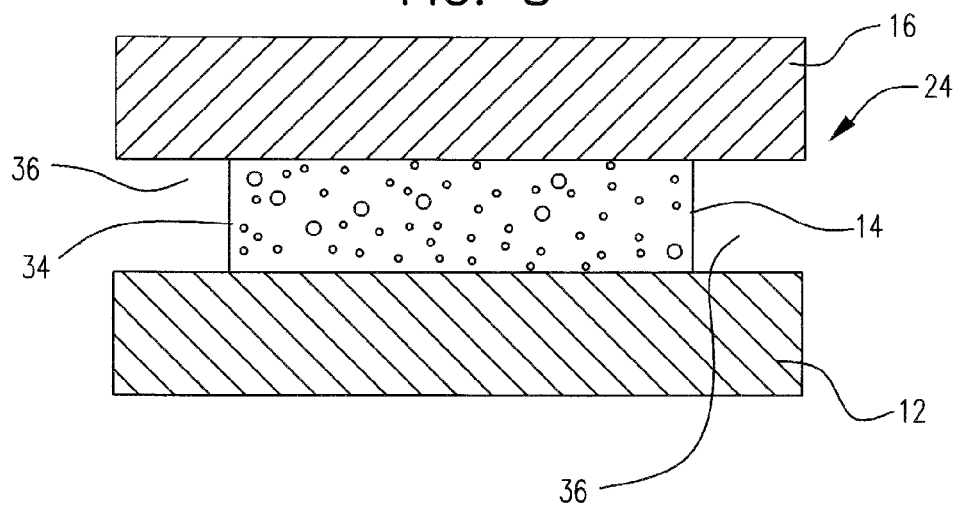
FIG. 8 is a side view of a stent strut similar to that shown in FIG. 7 after creating reservoirs for deposition of a drug in the intermediate layer.

In another aspect, reservoirs for depositing drug therein may be formed in the intermediate layer. In this embodiment, a nonporous intermediate layer 34 may be employed as shown in FIG. 7. A portion of the intermediate layer 34 can the be removed to form an under cut or cavity on the lateral wall, for example, by selectively etching the intermediate layer 34. Other methods include plasma etching and thermal dealloying. See, for example, U.S. Patent Pub. No. 2006/0193890, 2006/0193889 and 2006/0121080, each of which is incorporated by reference herein in its entirety. FIG. 8 illustrates the stent strut 24 after removal of some of the intermediate layer 34 to form reservoirs 36.

For such an embodiment, the at least one intermediate layer 34 may suitably be formed from a material that is different than that of the at least one support layer 12 or the at least one covering layer 16 so that the intermediate layer 34 can be selectively etched or electropolished in order to provide the cavities in that layer.

For example, a stent formed with support layer 12 and covering layer 16 of stainless steel, and intermediate layer 34 of gold, may be selectively etched with cyanide.

In another example, a support layer 12 and a covering layer 16 formed from a platinum-enhanced stainless steel alloy, and a stainless steel (316L) intermediate layer 34, may be etched with ferric chloride, nitric or sulfuric acid.

In yet another example, a support layer 12 and a covering layer 16 formed from a stainless steel (316L) and an intermediate layer 34 formed of titanium, may be selectively etched with hydrofluoric acid.

An etchant system typically includes a non-oxidizing acid, an oxidizing acid and dissolved metal. The principles of etching or electropolishing are well known in the art. In selecting the etching or electropolishing solution for selective etching of the intermediate layer, the following criteria may be considered:

1) addition of cation(s) to help passivate the metal to be protected;

2) addition of dissolved metal to prevent dissolution of the metal to be protected;

3) addition of an acid to selectively passivate or oxidize the metal to be protected; and 4) addition of an active conjugate base to assist protonation of the metal to be dissolved (halides);

5) select acid concentration to adjust the voltage of each metal to selectively activate reaction to one but not the other; and 6) employ the galvanic potential between the metals to activate dissolution of the more active metal.

In using criteria 2), for example, the etching solution can be saturated with the metal of the covering layer and the support layer in order to passivate or protect the metal or metal alloy of these layers.

For example, a solution of nitric acid ($HNO_3$) and ammonium bifluoride (ABF) is a broad based etching solution. Dissolving stainless steel (316L) metal ions in solution, can passivate a support layer and a covering layer of stainless steel, while etching a gold, tantalum or titanium intermediate layer, for example. The stainless steel ions can form passive oxides that slow down the metal dissolution rate.

Figure 9:
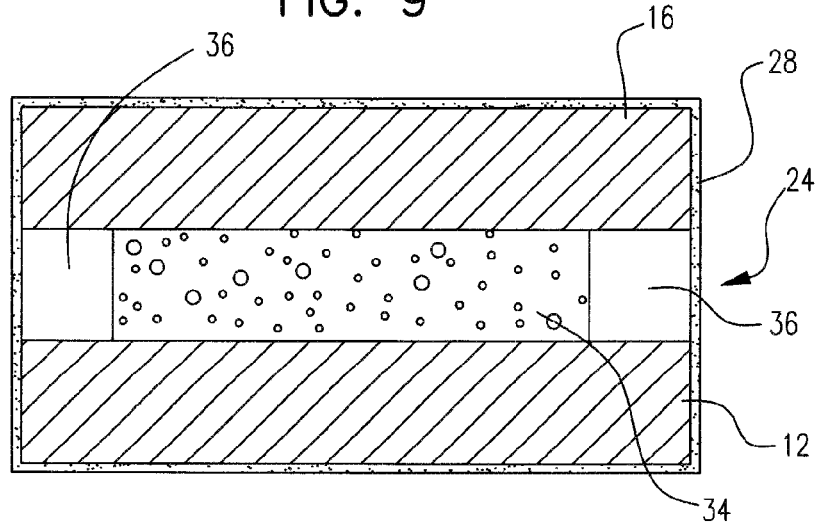
FIG. 9 is a side view of a stent strut similar to that shown in FIG. 8 with a coating thereon.

A coating 28 can be optionally applied to the stent after loading of the drug into the etched reservoirs as shown in FIG. 9.

The resultant stent elutes drug in a lateral direction as shown in FIGS. 3 and 4.

The above disclosure is intended to be illustrative and not exhaustive. This description will suggest many variations and alternatives to one of ordinary skill in this art. The various elements shown in the individual figures and described above may be combined or modified for combination as desired.

The invention claimed is:

1. A stent designed for the release of a drug, at least a portion of the stent comprising a multilayer structure, the multilayer structure comprising at least one outer layer formed of a first material, at least one inner layer formed of a second material, the second material is the same or different than the first material, the outer layer and the inner layer defining a stent wall, the stent further includes a central portion, a proximal end and a distal end and a lumen therebetween, the wall having openings extending therethrough, the multilayer structure further comprising at least one intermediate drug eluting layer disposed between the inner layer and the outer layer, the intermediate drug eluting layer comprises a metal, the intermediate drug eluting layer comprising channels therein, the channels having at least one therapeutic agent disposed therein, and wherein intermediate drug eluting layer elutes drug in a lateral direction.

2. The stent of claim 1 wherein said inner layer and said outer layer elute substantially no drug.

3. The stent of claim 1, said stent comprising said multilayer structure at least at said proximal end of said stent, at least at said distal end of or a combination thereof.

4. The stent of claim 1 wherein said stent is a bifurcated stent further comprising a branch portion in the central portion of the stent, said stent comprising said multilayer structure at least around said branch portion of said stent.

5. The stent of claim 1 wherein said intermediate layer is stainless steel, gold, tantalum or titanium.

6. The stent of claim 1 wherein said outer layer comprises at least one material selected from the group consisting of stainless steel, stainless steel enhanced with a platinum group metal, shape memory metals, cobalt-chromium alloys, radiopaque metals, and mixtures thereof.

7. The stent of claim 1 wherein said inner layer comprises at least one material selected from the group consisting of stainless steel, stainless steel enhanced with a platinum group metal, shape memory metals, cobalt-chromium alloys, radiopaque metals, and mixtures thereof.

8. The stent of claim 1 wherein said inner layer is stainless steel and said outer layer is stainless steel.

9. The stent of claim 1 wherein said inner layer is platinum enriched stainless steel and said outer layer is platinum enriched stainless steel.

10. The stent of claim 1 wherein said intermediate drug eluting layer elutes drugs in a lateral direction in at least some of the channels, from the distal end, from the proximal end or some combination thereof.

11. A stent designed for the release of a drug, at least a portion of the stent comprising a multilayer structure, the multilayer structure comprising at least one outer layer formed of a first material, at least one inner layer formed of a second material, the second material is the same or different than the first material, the outer layer and the inner layer defining a stent wall, the stent further a central portion, a proximal end and a distal end and a lumen therebetween, the wall having openings extending therethrough, the multilayer structure further comprising at least one intermediate drug eluting layer disposed between the inner layer and the outer layer, the intermediate drug eluting layer comprises a metal, the intermediate drug eluting layer comprising cavities therein, the cavities having at least one therapeutic agent disposed therein, and wherein intermediate drug eluting layer elutes drug in a lateral direction.

12. The stent of claim 11 wherein said inner layer and said outer layer elute substantially no drug.

13. The stent of claim 11, said stent comprising said multilayer structure at least at said proximal end of said stent, at least at said distal end of or a combination thereof.

14. The stent of claim 11 wherein said stent is a bifurcated stent further comprising a branch portion in the central portion of the stent, said stent comprising said multilayer structure at least around said branch portion of said stent.

15. The stent of claim 11 wherein said intermediate layer is stainless steel, gold, tantalum or titanium.

16. The stent of claim 11 wherein said outer layer and said inner layer comprises at least one material selected from the group consisting of stainless steel, stainless steel enhanced with a platinum group metal, shape memory metals, cobalt-chromium alloys, radiopaque metals, and mixtures thereof.

17. The stent of claim 11 wherein said inner layer is stainless steel and said outer layer is stainless steel.

18. The stent of claim 11 wherein said inner layer is platinum enriched stainless steel and said outer layer is platinum enriched stainless steel.

19. The stent of claim 11 wherein said intermediate drug eluting layer elutes drugs in a lateral direction in at least some of the cavities, from the distal end, from the proximal end or some combination thereof.

20. A stent designed for the release of a drug, the stent comprising a tubular structure and a stent wall, the stent wall having an inner surface, an outer surface, a proximal end and a distal end and a lumen extending therebetween defined by the inner surface of the stent wall, the stent wall having openings extending therethrough, the stent wall comprising channels or cavities which release drug in a lateral direction into at least some of the openings, from the proximal end, from the distal end or a combination thereof, the stent wall comprises a metal, the inner and outer surface of the stent wall is formed so as to release no therapeutic agent.

* * * * *